United States Patent
Bjork et al.

(10) Patent No.: US 12,391,907 B2
(45) Date of Patent: Aug. 19, 2025

(54) WATER-RECONSTITUTABLE CULTURE MEDIUM RESISTANT TO LIQUEFACTION BY MICROORGANISMS

(71) Applicant: NEOGEN FOOD SAFETY US HOLDCO CORPORATION, Lansing, MI (US)

(72) Inventors: Jason W. Bjork, Woodbury, MN (US); Sailaja Chandrapati, Woodbury, MN (US)

(73) Assignee: Neogen Food Safety US HoldCo Corporation, Lansing, MI (US)

( * ) Notice: Subject to any disclaimer, the term of this patent is extended or adjusted under 35 U.S.C. 154(b) by 564 days.

(21) Appl. No.: 16/771,866

(22) PCT Filed: Dec. 12, 2018

(86) PCT No.: PCT/IB2018/059939
§ 371 (c)(1),
(2) Date: Jun. 11, 2020

(87) PCT Pub. No.: WO2019/116259
PCT Pub. Date: Jun. 20, 2019

(65) Prior Publication Data
US 2020/0399574 A1 Dec. 24, 2020

Related U.S. Application Data

(60) Provisional application No. 62/597,961, filed on Dec. 13, 2017.

(51) Int. Cl.
| | |
|---|---|
| C12M 1/00 | (2006.01) |
| C08L 1/28 | (2006.01) |
| C12M 1/12 | (2006.01) |
| C12N 5/00 | (2006.01) |
| G05F 1/59 | (2006.01) |
| H02M 3/157 | (2006.01) |
| H02M 3/158 | (2006.01) |
| H02M 1/00 | (2006.01) |

(52) U.S. Cl.
CPC ............ *C12M 23/20* (2013.01); *C08L 1/284* (2013.01); *C12M 23/04* (2013.01); *C12N 5/0068* (2013.01); *G05F 1/59* (2013.01); *H02M 3/157* (2013.01); *H02M 3/1584* (2013.01); *H02M 1/0012* (2021.05)

(58) Field of Classification Search
None
See application file for complete search history.

(56) References Cited

U.S. PATENT DOCUMENTS

| | | | |
|---|---|---|---|
| 4,565,783 A | 1/1986 | Hansen | |
| 5,089,413 A * | 2/1992 | Nelson .................. | C12M 25/02 435/805 |
| 5,137,812 A | 8/1992 | Matner | |
| 5,232,838 A | 8/1993 | Nelson | |
| 5,364,766 A | 11/1994 | Mach | |
| 5,409,838 A | 4/1995 | Wickert | |
| 5,494,823 A | 2/1996 | Takemoto | |
| 5,601,998 A | 2/1997 | Mach | |
| 5,635,367 A | 6/1997 | Lund | |
| 5,681,712 A | 10/1997 | Nelson | |
| 5,723,308 A | 3/1998 | Mach | |
| 5,869,321 A | 2/1999 | Franklin | |
| 6,022,682 A | 2/2000 | Mach | |
| 6,632,661 B2 | 10/2003 | Wickert | |
| 7,087,401 B2 | 8/2006 | Sandberg | |
| 8,828,653 B2 | 9/2014 | Zook | |
| 8,828,682 B2 | 9/2014 | Mach | |
| 8,846,334 B2 | 9/2014 | Young | |
| 8,889,351 B2 | 11/2014 | Mach | |
| 9,273,340 B2 | 3/2016 | Moriyama | |

FOREIGN PATENT DOCUMENTS

| | | |
|---|---|---|
| WO | WO 2001-038559 | 5/2001 |
| WO | WO 2014-018433 | 1/2014 |
| WO | WO 2014-025514 | 2/2014 |
| WO | WO 2015-061213 | 4/2015 |

(Continued)

OTHER PUBLICATIONS

Turowski et al. "Prevention of metabolic diseases by HPMC, a non-fermentable fiber". Abstracts of Papers, 251st ACS National Meeting & Exposition, San Diego, CA, United States, Mar. 13-17, 2016 (2016), AGFD-193. American Chemical Society: Washington, D. C., p. 1.*

(Continued)

*Primary Examiner* — Vera Afremova
(74) *Attorney, Agent, or Firm* — HYLTON-RODIC LAW PLLC

(57) ABSTRACT

A device for growing microorganisms is provided. The device includes a body member comprising a self-supporting, waterproof substrate, a layer of adhesive disposed on the substrate, a powder adhered to the adhesive, a cover sheet adhered to the body member, and a dry composition including a mixture of hydroxypropylmethylcellulose and guar gum adhered to the cover sheet or the substrate. The powder comprises a cold-water-soluble gelling agent and one or more nutrient for growing microorganisms. The composition, when reconstituted with water, resists liquefaction by microorganisms A method of culturing microorganisms using the device is also provided.

8 Claims, 1 Drawing Sheet

(56) References Cited

FOREIGN PATENT DOCUMENTS

| WO | WO 2015-134686 |   | 9/2015 |
|----|----------------|---|--------|
| WO | WO 2015-134696 |   | 9/2015 |
| WO | WO 2016/085688 | * | 6/2016 |
| WO | WO 2016-176176 |   | 11/2016 |
| WO | WO 2016-176178 |   | 11/2016 |
| WO | WO 2016-176183 |   | 11/2016 |
| WO | WO 2017/019345 | * | 2/2017 |

OTHER PUBLICATIONS

International Search Report for PCT International Application No. PCT/IB2018/059939, mailed on Mar. 21, 2019, 5 pages.

\* cited by examiner

WATER-RECONSTITUTABLE CULTURE MEDIUM RESISTANT TO LIQUEFACTION BY MICROORGANISMS

CROSS REFERENCE TO RELATED APPLICATIONS

This application is a national stage filing under 35 U.S.C. 371 of PCT/IB2018/059939, filed Dec. 12, 2018, which claims the benefit of U.S. Provisional Application No. 62/597,961, filed Dec. 13, 2017, the disclosure of which are incorporated by reference in their entirety herein.

BACKGROUND

Media for culturing microorganisms are generally prepared by dispersing a solidifying agent in an aqueous solution containing nutrients and other ingredients necessary for the growth of specific microorganisms. Conventional solidifying agents, such as agar, are often inconvenient for the end user. Agar medium is typically prepared in bulk, sterilized, and then melted in boiling water or by exposure to flowing steam. The hot agar must be carefully cooled to approximately 45° C. before it can be poured into petri dishes. The cooled, but still liquefied, medium is aliquoted, poured into the petri dish containing the microbiological sample, mixed with the sample and allowed to solidify. After the agar hardens, the plates are incubated at a prescribed temperature for a prescribed period of time. After incubation, the number and variety of colonies growing in each dish is counted by visual inspection. In this way, one can determine the number and variety of microorganisms or colony-forming units present in an aqueous sample.

A dry culture medium device is disclosed in U.S. Pat. No. 4,565,783, entitled "Dry Culture Media," granted to Hansen (the '783 patent, which is incorporated herein by reference in its entirety). The device of the '783 patent comprises a bottom member with an adhesive coating and a further coating of cold-water-soluble powder adhered uniformly to the adhesive coating. The powder comprises one or more ingredients such as a gelling agent, one or more nutrients, or a mixture thereof. A preferred embodiment further comprises a cover sheet releasably adhered to at least a portion of the bottom member.

The '783 patent also discloses an embodiment of the device that employs a spacer attached to the upper surface of the substrate. The spacer has an aperture cut in its center that forms a well of predetermined size, shape and volume that is designed to confine the culture medium following hydration.

U.S. Pat. No. 6,022,682, entitled, "Article and Method for Detection of Enterotoxigenic Staphylococci," granted to Mach et al. (the '682 patent, which is incorporated herein by reference in its entirety) teaches the use of a disc-shaped article for detecting or confirming the presence of thermostable nuclease positive, potentially enterotoxigenic staphylococci in a sample. The article contains a chemical composition specific for the detection of specific strains of staphylococci. The article is particularly adapted for detecting the presence of enterotoxigenic staphylococci such as *S. aureus* in a pre-grown, gel-based bacterial culture.

Thin film culture devices provide a convenient alternative to traditional agar culture medium for growing and enumerating microorganisms. There exists a need for thin film culture devices having improvements over the state-of-the-art thin film culture devices.

SUMMARY

The present disclosure generally relates to thin film culture devices for growing, detecting, and enumerating microorganisms present in a sample material. In particular, the present disclosure relates to articles and methods to detect and enumerate microorganisms present in a sample that comprises at least one microorganism capable of disintegrating (e.g., via hydrolytic enzymes) a polymer hydrogel formed from a dry, cold-water-soluble gelling agent such as, for example, guar gum, locust bean gum, xanthan gum, or a mixture of any two or more of the foregoing gelling agents. Articles of the present disclosure comprise an effective amount of cold-water-soluble gelling agent that forms a hydrogel that is substantially resistant to disintegration by hydrolytic enzymes produced by certain bacteria and that does not substantially inhibit growth of a variety of microorganisms found in sample materials. Advantageously, the articles of the present disclosure provide improved accuracy and precision when used in methods of enumerating microorganisms present in a sample material.

In one aspect, the present disclosure provides an article. The article can comprise a body member comprising a self-supporting, water-proof substrate having upper and lower surfaces; a layer of adhesive disposed on the upper surface of the substrate, the adhesive being non-inhibitory to the growth of microorganisms; a cold-water-soluble powder adhered to the adhesive; a cover sheet having an inner-facing surface and an outer-facing surface, the cover sheet adhered to at least a portion of the body member; and a dry composition comprising a mixture of hydroxypropylmethylcellulose and guar gum adhered to the inner-facing surface of the cover sheet or the upper surface of the body member. The cold-water-soluble powder can comprise a cold-water-soluble gelling agent and one or more nutrients for growing microorganisms. The device includes a microbial growth zone disposed between the substrate and the cover sheet. The microbial growth zone is free of matrixes that prevent visualization of bacterial colonies. The cover sheet is adhered to the body member so that the upper surface of the substrate faces the inner-facing surface of the cover sheet. In any embodiment, the cold-water-soluble powder can comprise guar gum and hydroxypropylmethylcellulose. In any embodiment, the cold-water-soluble gelling agent can consist essentially of guar gum and hydroxypropylmethylcellulose.

In any of the above embodiments wherein the cold-water-soluble powder includes hydroxypropylmethylcellulose and guar gum, the hydroxypropylmethylcellulose and guar gum can be present in the cold-water-soluble gelling agent at a mass ratio of greater than or equal to one part hydroxypropylmethylcellulose to one part guar gum. In any of the above embodiments wherein the cold-water-soluble gelling powder includes hydroxypropylmethylcellulose and guar gum, the hydroxypropylmethylcellulose and guar gum can be present in the cold-water-soluble gelling agent at a mass ratio of less than or equal to three parts hydroxypropylmethylcellulose to one part guar gum.

In another aspect, the present disclosure provides an article. The article can comprise a body member comprising a self-supporting, water-proof substrate having upper and lower surfaces; a cold-water-reconstitutable coating adhered to the upper surface of the substrate; a cover sheet having an inner-facing surface and an outer-facing surface, the cover sheet adhered to at least a portion of the body member; and a dry composition comprising a mixture of hydroxypropylmethylcellulose and guar gum adhered to the inner-facing surface of the cover sheet or the upper surface of the body member. The cold-water-soluble powder can comprise a cold-water-soluble gelling agent and one or more nutrients for growing microorganisms. The device includes a microbial growth zone disposed between the substrate and the cover sheet. The microbial growth zone is free of matrixes that prevent visualization of bacterial colonies. The cover sheet is adhered to the body member so that the upper surface of the substrate faces the inner-facing surface of the cover sheet. In any embodiment, the cold-water-reconstitutable coating can comprise guar gum and hydroxypropylmethylcellulose. In any embodiment, the cold-water-reconstitutable coating can consist essentially of guar gum and hydroxypropylmethylcellulose. In any of the above embodiments wherein the cold-water-reconstitutable coating includes hydroxypropylmethylcellulose and guar gum, the hydroxypropylmethylcellulose and guar gum can be present in the coating at a mass ratio of greater than or equal to one part hydroxypropylmethylcellulose to one part guar gum. In any of the above embodiments wherein the cold-water-reconstitutable coating powder includes hydroxypropylmethylcellulose and guar gum, the hydroxypropylmethylcellulose and guar gum can be present in the coating at a mass ratio of less than or equal to three parts hydroxypropylmethylcellulose to one part guar gum.

In any of the above embodiments, the dry composition further can comprise guar gum. In any of the above embodiments wherein the dry composition includes guar gum, the dry composition can consist essentially of hydroxypropylmethylcellulose and guar gum. In any of the above embodiments wherein the dry composition includes guar gum, the hydroxypropylmethylcellulose and guar gum can be present in the dry composition at a mass ratio of greater than or equal to one part hydroxypropylmethylcellulose to one part guar gum. In any of the above embodiments wherein the dry composition includes guar gum, the hydroxypropylmethylcellulose and guar gum can be present in the dry composition at a mass ratio of less than or equal to three parts hydroxypropylmethylcellulose to one part guar gum.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a coating comprising "a" gelling agent can be interpreted to mean that the coating can comprise "one or more" gelling agents.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The features and advantages of the present invention will be understood upon consideration of the detailed description of the preferred embodiment as well as the appended claims. These and other features and advantages of the invention may be described below in connection with various illustrative embodiments of the invention.

The above summary of the present invention is not intended to describe each disclosed embodiment or every implementation of the present invention. The Figures and the detailed description which follow more particularly exemplify illustrative embodiments. Other features, objects and advantages will become apparent from the description and drawings, and from the claims.

BRIEF DESCRIPTION OF DRAWINGS

The invention may be further illustrated by reference to the accompanying drawings wherein.

Figure 1:
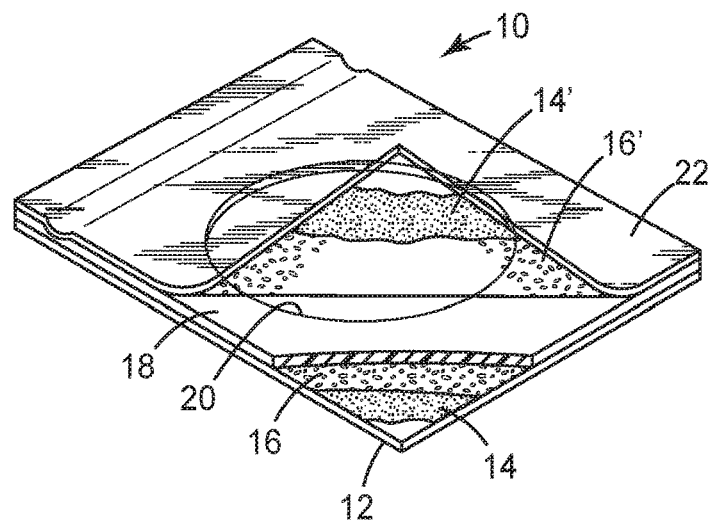
FIG. 1 is a top perspective view, partially in section, of a preferred microbiological growing device of the invention.

While the above-identified drawing figures set forth several embodiments of the disclosure, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to culture devices (e.g., thin film culture devices) for growing, detecting, and enumerating microorganisms present in a sample material. Methods of growing, detecting, and enumerating microorganisms present in a sample material are also provided.

Suitable sample materials can be obtained or derived from a variety of sources. The term "source" is generally used to refer to the food or nonfood desired to be tested for microorganisms. The source can be a solid, a liquid, a semi-solid, a gelatinous material, gas (e.g., air), and combinations thereof. In some embodiments, the source can be provided by a capture element that was used, for example, to collect the source from a surface of interest or from air. In some embodiments, the liquid composition can include the capture element, which can be further broken apart (e.g., during an agitation or dissolution process) to enhance retrieval of the source and any microorganism of interest. The surface of interest can include at least a portion of a variety of surfaces, including, but not limited to, walls (including doors), floors, ceilings, drains, refrigeration systems, ducts (e.g., air ducts), vents, toilet seats, handles, doorknobs, handrails, countertops, tabletops, eating surfaces (e.g., trays, dishes, etc.), working surfaces, equipment surfaces, clothing, etc., and combinations thereof. All or a portion of the source can be used in the method. When a portion of the source is used, this can sometimes be referred to as a "sample" of the source. However, the term "sample" is generally used herein to refer to the portion of volume or mass of material that is obtained from the source and is introduced into a test device for the detection of microorganisms.

The term "food" is generally used to refer to a solid, liquid (e.g., including, but not limited to, solutions, dispersions, emulsions, suspensions, etc., and combinations thereof) and/or semi-solid comestible composition. Examples of foods include, but are not limited to, meats, poultry, eggs, fish, seafood, vegetables, fruits, prepared foods (e.g., soups, sauces, pastes), grain products (e.g., flour, cereals, breads), canned foods, milk, other dairy products (e.g., cheese, yogurt, sour cream), fats, oils, desserts, condiments, spices, pastas, beverages, water, beer, animal feed, other suitable comestible materials, and combinations thereof.

One type of thin film culture devices known in the art, comprising two adjoined sheets with dry culture medium adhered therebetween, is described in U.S. Pat. No. 4,565,783. These devices are useful for growing, detecting, and enumerating a variety of microorganisms including, for example, total aerobic bacteria or coliform bacteria. U.S. Pat. No. 5,137,812; which is incorporated herein by reference in its entirety; describes a thin film culture device and a method of deriving a colony blot therefrom in order to detect a microorganism (*Escherichia coli* 0157) using an immunospecific indicator reagent.

Figure 4:
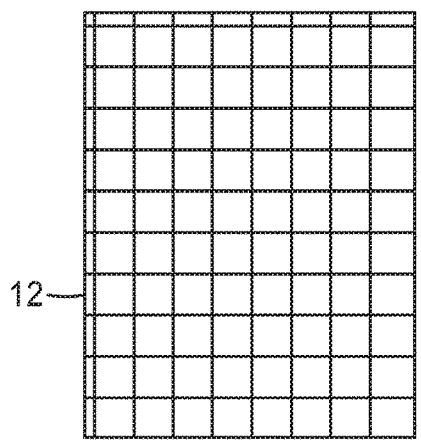
FIG. 4 is a top view of the device of FIG. 2 showing a grid pattern printed on the substrate.

FIGS. 1 and 4 illustrate one embodiment of a device in accordance with the present disclosure. The microbiological growing device 10 includes a body member comprising a self-supporting water-proof substrate 12 having upper and lower surfaces. Substrate 12 is preferably a relatively stiff film of a material such as polyester, polypropylene or polystyrene which will not absorb or otherwise be affected by water. Polyester films approximately 0.1 mm to 0.18 mm thick, polypropylene films approximately 0.1 mm to 0.2 mm thick and polystyrene films approximately 0.38 mm thick have been found to work well. Other suitable substrates include photoprint paper with a polyethylene or other waterproof coating, as described in U.S. Pat. No. 4,565,783. The substrate 12 may be either transparent or opaque, depending on whether one wishes to view bacterial colonies through the substrate. To facilitate the counting of bacterial colonies, the substrate 12 may have a pattern (e.g., a square grid pattern) printed thereon as shown in FIG. 4.

Substrate 12 is coated on its upper surface with a layer of an adhesive 14 which serves to hold a cold-water-soluble powder 16 on the substrate in a uniform monolayer for easy hydration. Adhesive 14 preferably is water-insoluble and non-inhibitory to the growth of microorganisms. Preferably, the adhesive is sufficiently transparent when wet to enable the viewing of bacterial colonies through the film coated with the adhesive. Suitable adhesives for use in adhesive 14 include, for example, pressure-sensitive adhesives. However, heat-activated adhesives wherein a lower melting substance is coated onto a higher melting substance may also be used. Water-activated adhesives such as mucilage may also be useful.

Adhesive 14 should be coated onto substrate 12 in a thickness which is preferably less than the diameter of the particles of the powdered gelling agent and/or nutrients. In any embodiment, it may be preferable to apply enough adhesive to adhere the particles to the substrate but not so much that the particles become completely embedded in the adhesive. A uniform monolayer of powder 16 is desired to ensure uniformity of the rehydrated culture media. The dry powder coating should have sufficient surface area exposed in a microbial growth zone for hydration during use. Generally, an adhesive layer in the thickness range of about 5 µm to about 13 µm is suitable.

The microbial growth zone is the region in the device into which the sample is placed during inoculation of the device. Typically, the microbial growth zone is spaced apart from the edges of the substrate 12 and the cover sheet (described herein) in order to prevent contamination of the sample and/or prevent leakage of the sample out of the device. After an aqueous liquid (e.g., containing the sample to be tested) is placed into the microbial growth zone, the cold-water-soluble powder and the dry composition are contacted by the liquid. The microbial growth zone is free of matrixes that prevent visualization of bacterial colonies.

A non-limiting example of an adhesive suitable for use in a device of the present disclosure is a copolymer of isooctylacrylate/acrylamide (in a mole ratio of 94/6). Other pressure sensitive adhesives which may be used include isooctylacrylate/acrylic acid (in a mole ratio of 95/5 or 94/6) and silicone rubber. Adhesives which turn milky upon exposure to water are less preferred, but may be used in conjunction with a nontransparent substrate or where colony visualization is not required.

A monolayer of cold-water-soluble powder 16 is adhered uniformly to adhesive layer 14. Powder 16 comprises at least one ingredient selected from the group consisting of a cold-water-soluble gelling agent one or more nutrients for growing microorganisms, and a mixture of a cold-water-soluble gelling agent and one or more nutrients for growing microorganisms. As used in the specification and claims, the term "powder" designates a finely divided particulate material having an average diameter of less than 400 micrometers. As used in the specification and claims, the term "cold-water-soluble" designates material which forms a solution in water at room temperature.

The "cold-water-solubility" of the powders employed in the devices of the present invention may result, for example, from the inclusion in these powders of an appropriate gelling agent. Suitable gelling agents for inclusion in powder 16 include both natural and synthetic gelling agents which form solutions in water at room temperature. Gelling agents such as hydroxypropylmethylcellulose, hydroxyethyl cellulose, carboxymethyl cellulose, polyacrylamide, locust bean gum and agar form solutions in water at room temperature and are suitable gelling agents for providing powders which are "cold-water-soluble." In any embodiment, the cold-water-soluble gelling agent may comprise hydroxypropylmethylcellulose. Preferred gelling agents for powder 16 include, for example, guar gum and xanthan gum, these gelling agents being useful individually or in combination with one another and in combination with hydroxypropylmethylcellulose. Nutrients for growing microorganisms form solutions in water at room temperature.

In particularly-preferred embodiments, the cold-water-soluble gelling agent comprises guar gum and hydroxypropylmethylcellulose. In any embodiment, the cold-water-soluble gelling agent can consist essentially of guar gum and hydroxypropylmethylcellulose.

In any embodiment wherein hydroxypropylmethylcellulose and guar gum are present in the cold-water-soluble gelling agent, they may be present in the cold-water-soluble gelling agent at a mass ratio of less than or equal to one part hydroxypropylmethylcellulose to one part guar gum. In any embodiment wherein hydroxypropylmethylcellulose and guar gum are present in the cold-water-soluble gelling agent, they may be present in the cold-water-soluble gelling agent at a mass ratio of less than or equal to three parts hydroxypropylmethylcellulose to one part guar gum.

In any embodiment, the cold-water-soluble powder can comprise powdered nutrients and powdered cold-water-soluble gelling agent(s) that are present in a ratio of about 3 parts nutrients:1 part cold-water-soluble gelling agent(s).

As indicated, cold-water-soluble powder 16 may comprise only a gelling agent. Where the device, as manufactured, contains a powder comprising only gelling agent, the end user adds his own special nutrients "tailored" to the type of microorganisms he wishes to grow. For example, dry powdered nutrients may be suspended in a rapidly evaporating liquid as ethanol or "Freon". In other instances, dry powdered nutrients may be suspended or dissolved in aqueous solutions. An aliquot of the liquid is added to the surface of substrate 12 which has been coated previously with adhesive and gelling agent. The liquid is allowed to evaporate, leaving ample nutrients along with the gelling agent. In other instances, the dry powdered nutrient(s) may be suspended or dissolved in an aqueous liquid that is used to hydrate the dry powder. In these instances, the liquid is not evaporated before use. The sample may be mixed with the aqueous liquid before or shortly after the dry powder is hydrated with the aqueous liquid. Alternatively, the sample may be applied to the hydrated dry powder after the gelling agent has been hydrated and allowed to form a hydrogel.

Where gelling agent is included in powder 16, a sufficient amount of the gelling agent is adhered to the substrate so that a predetermined quantity of water or an aqueous sample, e.g., 1-3 milliliters, placed on the substrate will form a gel having a viscosity of about 1500 cps or more when measured at 60 rpm with a Brookfield Model LVF viscometer at 25° C. Gels of this viscosity will allow convenient handling and stacking and provide distinct colony identification. In most cases 0.025 to 0.050 gram of guar gum on a surface area of about 20 cm$^2$ will provide a sufficiently viscous gel when hydrated with 1-3 milliliters of an aqueous sample. The size of the powder particles can be used to control the coating weight per unit area. For example, approximately 100 mesh guar gum coats to a weight of about 0.05 grams/5 cm diameter disc; and a 400 mesh guar gum coats to a weight of about 0.025 grams/5 cm diameter disc. If additional amounts of gelling agent and/or nutrients are required, the optional cover sheet of this embodiment may also be coated.

One embodiment of a coating mixture for powder 16 is as follows:
15 grams guar gum or xanthan gum
5 grams peptone
2.5 grams yeast extract
1 gram dextrose
0.06 gram sodium carbonate
0.12 gram "Cab-O-Sil M-5" (a fumed silicon dioxide, commercially available from Cabot Corporation)

The aforementioned components of the powder mixture can be blended together and dusted onto an adhesive-coated substrate, for example, as described in Example 1 of U.S. Pat. No. 4,565,783.

Sodium carbonate is employed to provide a medium exhibiting a neutral pH. "Cab-0-Sil M-5" is employed as a processing aid. Of course, the particular coating mixture used for powder 16 may depend upon the type of microorganisms to be grown.

In preparing a coating mixture comprising the above ingredients, the peptone, yeast extract, dextrose and sodium carbonate are dissolved in water and the resulting solution can be spray-dried by conventional means to give a homogeneous mixture of the ingredients. The remaining ingredients are then combined with the above mixture to provide the final coating mixture.

It may be desirable to incorporate a dye into the medium mixture. Alternatively, the dye may be incorporated in adhesive 14. Suitable dyes are those which are metabolized by the growing microorganisms, and which cause the colonies to be colored for easier visualization. Examples of such dyes include triphenyl tetrazolium chloride, p-tolyl tetrazolium red, tetrazolium violet, veratryl tetrazolium blue and related dyes. Other suitable dyes are those sensitive to pH changes (e.g., neutral red, carboxyphenol red), chromogenic enzyme substrates, and fluorogenic enzyme substrates.

It is also contemplated within the scope of the invention that powder 16 may optionally include reagents necessary for carrying out certain microbiological tests. For example, antibiotics may be included for carrying out antibiotic susceptibility tests. For microorganism identification, reagents such as those which undergo a color change in the presence of a particular type of microorganism may be included.

In the device of FIG. 1, the body member includes a spacer element applied to the upper surface of substrate 12, the spacer element comprising a piece of spacer 18 having a circular aperture 20 cut through the center to expose the powder 16 on substrate 12. The walls of aperture 20 provide a well of predetermined size and shape to confine the medium following hydration. Spacer 18 should be thick enough to form a well of the desired volume, e.g., 1, 2 or 3 milliliter. Closed cell polyethylene foam is preferred material for spacer 18, but any material which is hydrophobic (non-wetting), inert to microorganisms, and capable of withstanding sterilization may be used. In these embodiments, the aperture 20 typically forms a perimeter of the microbial growth zone in the culture device.

Adhered to one edge of spacer 18 of the body member is a cover sheet 22. Cover sheet 22 is preferably transparent to facilitate counting of the bacterial colonies and is substantially impermeable to bacteria and water vapor. As used in the specification and claims, "substantially impermeable to bacteria and moisture vapor" designates cover sheets which prevent undesired contamination of the dehydrated medium during shipping, storage and use of the devices and which provide an environment which will support the growth of microorganisms during the incubation period. Generally, it will have the same properties as substrate 12, but need not be as stiff. Cover sheet 22 can be selected to provide the amount of oxygen transmission necessary for the type of microorganism desired to be grown. For example, polyester films have a low oxygen permeability (less than 5 g/645 cm$^2$/24 hours per 0.025 mm of thickness) and would be suitable for growing anaerobic bacteria. On the other hand, polyethylene has a very high oxygen permeability (approximately 500 g/645 cm$^2$/24 hours per 0.025 mm of thickness)

and would be suitable for aerobic organisms. The presently preferred material for cover sheet 22 is a 1.6 mil biaxially-oriented polypropylene film. Cover sheet 22, as illustrated, is coated with optional layers of adhesive 14' and powder 16'. It is to be understood that cover sheet 22 may alternatively be adhered to substrate 12 of the body member and that it may be free of any coating or may be coated with a layer of pressure-sensitive adhesive only.

Figure 2:
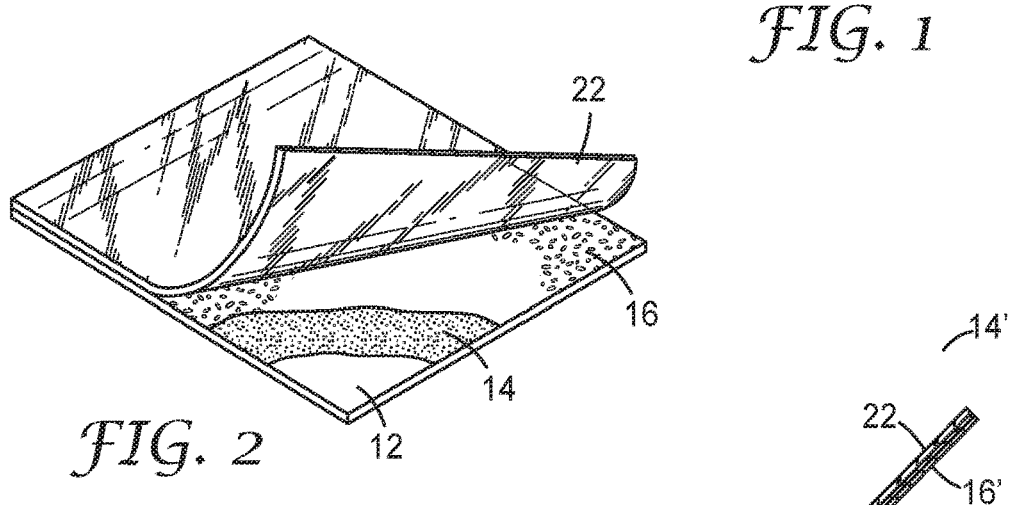
FIG. 2 is a top perspective view of an alternative embodiment of the invention.

The embodiment of FIG. 2 is identical to that of FIG. 1 except that spacer 18 is not present. A template, such as a weighted circular ring, may be applied temporarily to the outside of cover sheet 22, after closing, to confine the gel to a specific region (i.e., the microbial growth zone of the culture device).

Although both of the embodiments illustrated in the drawing have a cover sheet 22 attached to the device, it is also contemplated within the scope of the invention that the powder-containing embodiments may be uncovered and simply placed in a sterile environment during storage and incubation.

Another device (not illustrated) in accordance with the present invention comprises a bottom member comprising a self-supporting, water-proof substrate having upper and lower surfaces. Coated on at least a portion of the upper surfaces of the substrate is a coating which is substantially water-free and which consists essentially of a cold-water-reconstitutable material comprising at least one ingredient selected from the group consisting of a cold-water-soluble gelling agent, one or more nutrients for growing microorganisms, and a mixture of a cold-water-soluble gelling agent and one or more nutrients for growing microorganisms. As used in the specification and claims, the phrase "substantially water-free" designates a coating which has a water content no greater than about the water content of the dehydrated coating once it has been permitted to equilibrate with the ambient environment.

Suitable substrates for employment as the body member in this embodiment include those discussed above in connection with the illustrated embodiments.

This embodiment also comprises a cover sheet releasably adhered to at least a portion of the bottom member, the cover sheet being substantially impermeable to bacteria and water vapor. The cover sheet may be coated with dry composition that may include a gelling agent and/or nutrient mixture in the form of, for example, the above-described cold-water-soluble powder adhered to the cover sheet by means of an adhesive layer or a coating such as that which is coated on the substrate of the body member in this embodiment. In any embodiment, the dry composition adhered to the cover sheet can comprise hydroxypropylmethylcellulose. Alternatively, the cover sheet may also be coated with only a pressure-sensitive adhesive or may be free of any type of coating. Suitable materials for the cover sheet include those discussed above in connection with the illustrated embodiments.

In any embodiment of a device according to the present disclosure, the dry composition adhered to the cover sheet may comprise a second cold-water-soluble gelling agent (e.g., guar gum). In these embodiments, the dry composition can have a ratio of hydroxypropylmethylcellulose:second cold-water-soluble gelling agent.

The material employed in the coating of this embodiment is cold-water-reconstitutable. As used in the specification and claims, "cold-water-reconstitutable" designates material which forms a solution, sol or gel in water at room temperature. Suitable gelling agents for inclusion in the coating of this embodiment (if such are contained in the coating) include the above-described gelling agents which form solutions in water at room temperatures. In addition, it has been found that agar, after it has been dissolved in boiling water and deposited as a coating, is a material which is "cold-water-reconstitutable".

A preferred coating mixture for providing the coating of this embodiment is prepared by mixing the following ingredients:

15 grams agar
32.7 grams peptone
16.3 grams yeast extract
6.5 grams dextrose
2.0 grams "Guar M150" (a polysaccharide, commercially available from Celanese Corporation)
0.1 gram sodium carbonate
0.2 gram "TRITON X-100" (a wetting agent, commercially available from Rohm and Haas)
1000 grams water The aforementioned components can be mixed together, coated onto a substrate and dried, for example, as described in Example 12 of U.S. Pat. No. 4,565,783. In any embodiment, the cold-water-reconstitutable coating can comprise nutrients and cold-water-soluble gelling agent(s) that are present in a ratio of about 1 part nutrients:2 parts cold-water-soluble gelling agent(s). In any embodiment, the cold-water-reconstitutable coating may be adhered to the substrate by applying the coating to an adhesive layer adhered to the substrate, as described herein.

The coating may optionally include dyes, antibiotics and cross-linking agents, examples of such ingredients including those described hereinabove.

The body member of this embodiment may optionally comprise a spacer element applied to the substrate, examples of suitable spacer elements including those discussed above in connection with the illustrated embodiments. In the event such a spacer element is present, the cover sheet may be, for example, releasably adhered to the spacer element.

Figure 3:
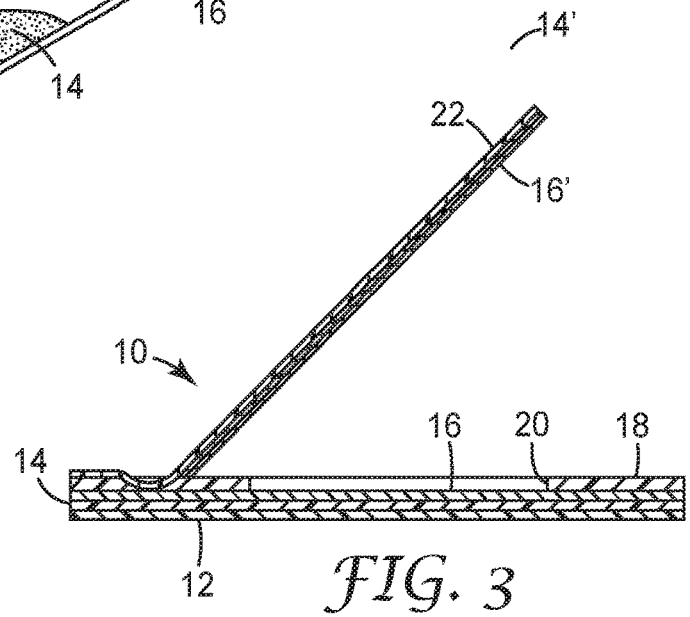
FIG. 3 is a cross sectional view of device of FIG. 1.

The use of the devices of the present invention will be discussed with specific reference to the device of FIGS. 1 and 3. To use the device of FIGS. 1 and 3 as a pour plate, cover sheet 22 is pulled back and a predetermined quantity of water or an aqueous test sample is placed on substrate 12 of the body member. The gelling agent and/or nutrients adhered to substrate 12 by adhesive 14 are quickly hydrated or dissolved and a nutrient gel is formed. Cover sheet 22 is then replaced over the substrate, and a weighted plate placed on top to spread the sample completely. The device is then incubated for a predetermined period of time. Any bacterial colonies growing in the medium can be counted through the transparent cover film.

The device may also be conveniently used for "Rodac" testing wherein the surfaces of various objects are examined to determine the extent of bacterial contamination. Cover sheet 22 coated only with a pressure sensitive adhesive is pulled back and touched to the surface being tested. The adhesive picks up any microorganisms from the surface being tested. The device is then hydrated, cover sheet 22 replaced, and the device incubated.

Thin film culture devices according to the present disclosure may include nutrients, indicator reagents and, optionally, selective agents chosen to detect/enumerate a particular microorganism or group of microorganisms.

Thin film culture devices have been used to grow and enumerate aerobic bacteria, anaerobic bacteria, and/or bacteria from dairy samples, for example, as described in U.S. Pat. No. 4,565,783. It is contemplated that, in some embodiments, thin film culture devices according to the present disclosure; which comprise hydroxypropylmethylcellulose as at least a portion of material(s) that react with an aqueous solvent in the device to form a hydrogel in the device and which employ nutrients, selective agents, indicators, and incubation conditions as taught by U.S. Pat. No. 4,565,783; can also be used to grow and enumerate aerobic bacteria, anaerobic bacteria, and/or bacteria from dairy samples, for example.

Thin film culture devices have been used to grow and enumerate aerobic microorganisms including yeast and mold, for example; as described in U.S. Pat. No. 5,089,413, which is incorporated herein by reference in its entirety. It is contemplated that, in some embodiments, thin film culture devices according to the present disclosure; which comprise hydroxypropylmethylcellulose as at least a portion of material(s) that react with an aqueous solvent in the device to form a hydrogel in the device and which employ nutrients, selective agents, indicators, and incubation conditions as taught by U.S. Pat. No. 5,089,413; can also be used to grow and enumerate aerobic microorganisms including yeast and mold, for example.

Thin film culture devices have been used to grow and enumerate colonies of microorganisms (e.g., species of *E. coli*) and the colonies have subsequently been transferred (e.g., "blotted") onto a membrane for identification of the microorganisms, for example, as described in U.S. Pat. No. 5,137,812; which is incorporated herein by reference in its entirety. It is contemplated that, in some embodiments, thin film culture devices according to the present disclosure; which comprise hydroxypropylmethylcellulose as at least a portion of material(s) that react with an aqueous solvent in the device to form a hydrogel in the device and which employ nutrients, selective agents, indicators, and incubation conditions as taught by U.S. Pat. No. 5,137,812; can also be used to grow and enumerate colonies of microorganisms that are subsequently transferred (e.g., "blotted") onto a membrane for identification of the microorganisms.

Thin film culture devices comprising a layer of water-based adhesive composition (for example), as described in U.S. Pat. No. 5,232,838; which is incorporated herein by reference in its entirety) have been used to detect and enumerate microorganisms present in larger-volume (e.g., >1 mL) aqueous samples. It is contemplated that, in some embodiments, thin film culture devices according to the present disclosure; which comprise hydroxypropylmethylcellulose as at least a portion of material(s) that react with an aqueous solvent in the device to form a hydrogel in the device and which employ nutrients, selective agents, indicators, and incubation conditions as taught by U.S. Pat. No. 5,232,838; can also be used to grow and enumerate colonies of microorganisms present in larger-volume (e.g., >1 mL) aqueous samples.

Thin film culture devices have been used for rapid detection and enumeration of coliform bacteria, for example, as described in U.S. Pat. Nos. 5,364,766 and 5,723,308; which each is incorporated herein by reference in its entirety. It is contemplated that, in some embodiments, thin film culture devices according to the present disclosure; which comprise hydroxypropylmethylcellulose as at least a portion of material(s) that react with an aqueous solvent in the device to form a hydrogel in the device and which employ nutrients, selective agents, indicators, and incubation conditions as taught by U.S. Pat. Nos. 5,364,766 and 5,723,308; can also be used rapidly to grow and enumerate colonies of coliform microorganisms present in a sample.

Thin film culture devices, having a pressure sensitive adhesive coating that includes a water-insoluble organic acid to stabilize indicator dyes disposed in the device, have been used for detection and enumeration of microorganisms, as described in U.S. Pat. No. 5,409,838; which is incorporated herein by reference in its entirety. It is contemplated that, in some embodiments, thin film culture devices according to the present disclosure; which comprise hydroxypropylmethylcellulose as at least a portion of material(s) that react with an aqueous solvent in the device to form a hydrogel in the device and which employ nutrients, selective agents, indicators, pressure sensitive adhesives comprising water-insoluble organic acids, and incubation conditions as taught by U.S. Pat. No. 5,409,838; can also be used to grow and enumerate colonies of microorganisms present in a sample.

Thin film culture devices, having an absorbent fibrous sheet to receive and distribute a liquid sample deposited therein, have been used to grow and enumerate microorganisms; as described in U.S. Pat. No. 5,494,823, which is incorporated herein by reference in its entirety. It is contemplated that, in some embodiments, thin film culture devices according to the present disclosure; which comprise hydroxypropylmethylcellulose as at least a portion of material(s) that react with an aqueous solvent in the device to form a hydrogel in the device and which employ absorbent fibrous sheets, nutrients, selective agents, indicators, and incubation conditions as taught by U.S. Pat. No. 5,494,823; can also be used to grow and enumerate microorganisms.

Thin film culture devices have been used to grow and enumerate bacteria of the Enterobacteriaceae family of Gram-negative microorganisms, for example, as described in U.S. Pat. No. 5,601,998; which is incorporated herein by reference in its entirety. It is contemplated that, in some embodiments, thin film culture devices according to the present disclosure; which comprise hydroxypropylmethylcellulose as at least a portion of material(s) that react with an aqueous solvent in the device to form a hydrogel in the device and which employ nutrients, selective agents, indicators, and incubation conditions as taught by U.S. Pat. No. 5,601,998; can also be used to grow and enumerate bacteria of the Enterobacteriaceae family of Gram-negative microorganisms.

Thin film culture devices have been used to grow and enumerate bacteria of the genus *Staphylococcus*, for example, as described in U.S. Pat. Nos. 5,635,367 and 7,087,401; each of which is incorporated herein by reference in its entirety. It is contemplated that, in some embodiments, thin film culture devices according to the present disclosure; which comprise hydroxypropylmethylcellulose as at least a portion of material(s) that react with an aqueous solvent in the device to form a hydrogel in the device and which employ nutrients, selective agents, indicators, and incubation conditions as taught by U.S. Pat. Nos. 5,635,367 and 7,087,401; can also be used to grow and enumerate bacteria of the genus *Staphylococcus*.

Thin film culture devices, having a water-insoluble spacer dimensioned to provide a head space that is configured to order to grow microbial colonies on the surface of a nutrient medium in the device, have been used to grow and enumerate microorganisms; as described, for example, in U.S. Pat. No. 5,681,712, which is incorporated herein by reference in its entirety. It is contemplated that, in some embodiments, thin film culture devices according to the present disclosure; which comprise hydroxypropylmethylcellulose as at least a portion of material(s) that react with an aqueous solvent in the device to form a hydrogel in the device and which employ water-insoluble spacers, nutrients, selective agents, indicators, and incubation conditions as taught by U.S. Pat. No. 5,681,712; can also be used to grow and enumerate microorganisms.

Thin film culture devices containing granulated medium particles have been used for detection and enumeration of microorganisms, as described in U.S. Pat. No. 5,869,321; which is incorporated herein by reference in its entirety. It is contemplated that, in some embodiments, thin film culture devices according to the present disclosure; which comprise hydroxypropylmethylcellulose as at least a portion of material(s) that react with an aqueous solvent in the device to form a hydrogel in the device and which employ nutrients, selective agents, indicators, granulated medium particles, and incubation conditions as taught by U.S. Pat. No. 5,869,321; can also be used to grow and enumerate colonies of microorganisms present in a sample.

Self-spreading thin film culture devices have been used for detection and enumeration of microorganisms, for example, as described in U.S. Pat. No. 6,632,661; which is incorporated herein by reference in its entirety. It is contemplated that, in some embodiments, thin film culture devices according to the present disclosure; which comprise hydroxypropylmethylcellulose as at least a portion of material(s) that react with an aqueous solvent in the device to form a hydrogel in the device and which are self-spreading and employ nutrients, selective agents, indicators, granulated medium particles, and incubation conditions as taught by U.S. Pat. No. 6,632,661; can also be used to grow and enumerate colonies of microorganisms present in a sample.

Thin film culture devices have been used to grow and, in concert with a dry article having a coating comprising toluidine blue O and unhydrolyzed nucleotides, have been used to enumerate enterotoxigenic bacteria of the genus *Staphylococcus*, for example, as described in U.S. Pat. No. 6,022,682; which is incorporated herein by reference in its entirety. It is contemplated that, in some embodiments, thin film culture devices according to the present disclosure; which comprise hydroxypropylmethylcellulose as at least a portion of material(s) that react with an aqueous solvent in the device to form a hydrogel in the device and which employ nutrients, selective agents, indicators, a dry article comprising toluidine blue O, and incubation conditions as taught by U.S. Pat. No. 6,022,682; can also be used to grow and enumerate enterotoxigenic bacteria of the genus *Staphylococcus*.

Thin film environmental sampling and culture devices have been used to grow and enumerate microorganisms present in environmental samples, for example, as described in U.S. Pat. No. 8,828,653; which is incorporated herein by reference in its entirety. It is contemplated that, in some embodiments, the environmental sampling and culture devices can be modified according to the present disclosure to hydroxypropylmethylcellulose as at least a portion of material(s) that react with an aqueous solvent in the device to form a hydrogel in the device. The modified environmental sampling and culture devices can employ nutrients, selective agents, indicators, and incubation conditions as taught by U.S. Pat. No. 8,828,653; to grow and enumerate microorganisms present in environmental samples.

Thin film culture devices have been used to grow and enumerate hemolytic microorganisms, for example, as described in U.S. Pat. No. 8,828,682; which is incorporated herein by reference in its entirety. It is contemplated that, in some embodiments, thin film culture devices according to the present disclosure; which comprise hydroxypropylmethylcellulose as at least a portion of material(s) that react with an aqueous solvent in the device to form a hydrogel in the device and which employ nutrients, selective agents, indicators, and incubation conditions as taught by U.S. Pat. No. 8,828,682; can also be used to grow and enumerate hemolytic microorganisms.

Thin film culture devices have been used to grow acid-producing hemolytic microorganisms, for example, as described in U.S. Pat. No. 8,846,334; which is incorporated herein by reference in its entirety. It is contemplated that, in some embodiments, thin film culture devices according to the present disclosure; which comprise hydroxypropylmethylcellulose as at least a portion of material(s) that react with an aqueous solvent in the device to form a hydrogel in the device and which employ nutrients, selective agents, indicators, and incubation conditions as taught by U.S. Pat. No. 8,846,334; can also be used to grow and enumerate hemolytic microorganisms.

Thin film culture devices have been used to grow microorganisms and, in concert with a dry article having a coating comprising methyl green and deoxyribonucleic acid, have been used to enumerate DNase-producing bacteria, for example, as described in U.S. Pat. No. 8,889,351; which is incorporated herein by reference in its entirety. It is contemplated that, in some embodiments, thin film culture devices according to the present disclosure; which comprise hydroxypropylmethylcellulose as at least a portion of material(s) that react with an aqueous solvent in the device to form a hydrogel in the device and which employ nutrients, selective agents, indicators, a dry article comprising methyl green and deoxyribonucleic acid, and incubation conditions as taught by U.S. Pat. No. 8,889,351; can also be used to grow and enumerate DNase-producing bacteria.

Thin film culture devices have been used to grow Enterobacteriaceae microorganisms and, in concert with a detection article having a coating comprising an indicator system, have been used to enumerate *Salmonella* bacteria in a sample, for example, as described in U.S. Pat. No. 9,273,340; which is incorporated herein by reference in its entirety. It is contemplated that, in some embodiments, thin film culture devices according to the present disclosure; which comprise hydroxypropylmethylcellulose as at least a portion of material(s) that react with an aqueous solvent in the device to form a hydrogel in the device and which employ nutrients, selective agents, indicators, a detection article comprising an indicator system, and incubation conditions as taught by U.S. Pat. No. 9,273,340; can also be used to grow and enumerate *Salmonella* bacteria.

Thin film culture devices have been used for rapid detection and enumeration of aerobic bacteria, for example, as described in International Publication No. WO2015/134696; which is incorporated herein by reference in its entirety. It is contemplated that, in some embodiments, thin film culture devices according to the present disclosure; which comprise hydroxypropylmethylcellulose as at least a portion of material(s) that react with an aqueous solvent in the device to form a hydrogel in the device and which employ nutrients, selective agents, indicators, and incubation conditions as taught by International Publication No. WO2015/134686; can also be used rapidly to grow and enumerate colonies of aerobic bacteria present in a sample.

Self-contained thin film culture devices have been used to generate a reduced-oxygen environment in situ for detection and enumeration of anaerobic bacteria or microaerophilic bacteria, for example, as described in International Publication Nos. WO2015/061213, WO2016/176183 and WO2016/176176; each of which is incorporated herein by reference in its entirety. It is contemplated that, in some embodiments, thin film culture devices according to the present disclosure;

which comprise hydroxypropylmethylcellulose as at least a portion of material(s) that react with an aqueous solvent in the device to form a hydrogel in the device and which employ nutrients, selective agents, indicators, and incubation conditions as taught by International Publication Nos. WO2015/061213, WO2016/176183 and WO2016/176176; can also be used to generate a reduced-oxygen environment in situ for detection and enumeration of anaerobic bacteria or microaerophilic bacteria.

Self-contained thin film culture devices have been used to generate a carbon dioxide-enriched environment in situ for detection and enumeration of capnophilic bacteria, for example, as described in International Publication No. WO2016/176178; which is incorporated herein by reference in its entirety. It is contemplated that, in some embodiments, thin film culture devices according to the present disclosure; which comprise hydroxypropylmethylcellulose as at least a portion of material(s) that react with an aqueous solvent in the device to form a hydrogel in the device and which employ nutrients, selective agents, indicators, and incubation conditions as taught by International Publication No. WO2016/176178; can also be used to generate a carbon dioxide-enriched environment in situ for detection and enumeration of capnophilic bacteria.

Self-contained thin film culture devices have been used to concentrate microorganisms from a large-volume sample into a smaller volume and to grow and enumerate the microorganisms present in the sample, for example, as described in International Publication No. WO2017/019345; which is incorporated herein by reference in its entirety. It is contemplated that, in some embodiments, thin film culture devices according to the present disclosure; which comprise hydroxypropylmethylcellulose as at least a portion of material(s) that react with an aqueous solvent in the device to form a hydrogel in the device and which employ nutrients, selective agents, indicators, and incubation conditions as taught by International Publication No. WO2017/019345; can also be used to concentrate microorganisms from a large-volume sample into a smaller volume and to grow and enumerate the microorganisms present in the sample.

The invention may be further illustrated by reference to the following non-limiting examples. All parts are expressed as parts by weight unless otherwise indicated.

EXEMPLARY EMBODIMENTS

Embodiment A is device for growing microorganisms, comprising:
a body member comprising a self-supporting, water-proof substrate having upper and lower surfaces;
a layer of adhesive disposed on the upper surface of the substrate, the adhesive being non-inhibitory to the growth of microorganisms;
a cold-water-soluble powder adhered to the adhesive, the powder comprising:
a cold-water-soluble gelling agent;
one or more nutrients for growing microorganisms;
a cover sheet having an inner-facing surface and an outer-facing surface, the cover sheet adhered to at least a portion of the body member; and
a dry composition comprising a mixture of hydroxypropylmethylcellulose and guar gum adhered to the inner-facing surface of the cover sheet or the upper surface of the body member;
wherein the device includes a microbial growth zone disposed between the substrate and the cover sheet;
wherein the microbial growth zone is free of matrixes that prevent visualization of bacterial colonies;
wherein the cover sheet is adhered to the body member so that the upper surface of the substrate faces the inner-facing surface of the cover sheet.

Embodiment B is the device of Embodiment A, wherein the cold-water-soluble powder comprises guar gum and hydroxypropylmethylcellulose.

Embodiment C is the device of Embodiment A, wherein the cold-water-soluble powder consists essentially of guar gum and hydroxypropylmethylcellulose.

Embodiment D is the device of Embodiment B or Embodiment C, wherein the hydroxypropylmethylcellulose and guar gum are present in the cold-water-soluble powder at a mass ratio of greater than or equal to one part hydroxypropylmethylcellulose to one part guar gum.

Embodiment E is the device of any one of Embodiments B through D, wherein the hydroxypropylmethylcellulose and guar gum are present in the cold-water-soluble powder at a mass ratio of less than or equal to three parts hydroxypropylmethylcellulose to one part guar gum.

Embodiment F is the device of any one of Embodiments B through E, wherein the dry composition consists essentially of hydroxypropylmethylcellulose and guar gum.

Embodiment G is the device of Embodiment F, wherein the hydroxypropylmethylcellulose and guar gum are present in the dry composition at a mass ratio of greater than or equal to one part hydroxypropylmethylcellulose to one part guar gum.

Embodiment H is the device of Embodiment F or Embodiment G, wherein the hydroxypropylmethylcellulose and guar gum are present in the dry composition at a mass ratio of less than or equal to three parts hydroxypropylmethylcellulose to one part guar gum.

Embodiment I is a device for growing microorganisms, comprising:
a body member comprising a self-supporting, water-proof substrate having upper and lower surfaces;
a cold-water-reconstitutable coating adhered to the upper surface of the substrate, the coating comprising:
a cold-water-soluble gelling agent;
one or more nutrients for growing microorganisms;
a cover sheet having an inner-facing surface and an outer-facing surface, the cover sheet adhered to at least a portion of the body member; and
a dry composition comprising a mixture of hydroxypropylmethylcellulose and guar gum adhered to the inner-facing surface of the cover sheet or the upper surface of the body member;
wherein the device includes a microbial growth zone disposed between the substrate and the cover sheet;
wherein the microbial growth zone is free of matrixes that prevent visualization of bacterial colonies;
wherein the cover sheet is adhered to the body member so that the upper surface of the substrate faces the inner-facing surface of the cover sheet.

Embodiment J is the device of Embodiment I, wherein the cold-water-reconstitutable coating comprises guar gum and hydroxypropylmethylcellulose.

Embodiment K is the device of Embodiment I, wherein the cold-water-reconstitutable coating consists essentially of guar gum and hydroxypropylmethylcellulose.

Embodiment L is the device of Embodiment J or Embodiment K, wherein the hydroxypropylmethylcellulose and guar gum are present in the cold-water-reconstitutable coating at a mass ratio of greater than or equal to one part hydroxypropylmethylcellulose to one part guar gum.

Embodiment M is the device of any one of Embodiments J through L, wherein the hydroxypropylmethylcellulose and guar gum are present in the cold-water-reconstitutable coating at a mass ratio of less than or equal to three parts hydroxypropylmethylcellulose to one part guar gum.

Embodiment N is the device of any one of Embodiments I through M, wherein the dry composition consists essentially of hydroxypropylmethylcellulose and guar gum.

Embodiment O is the device of Embodiment N, wherein the hydroxypropylmethylcellulose and guar gum are present in the dry composition at a mass ratio of greater than or equal to one part hydroxypropylmethylcellulose to one part guar gum.

Embodiment P is the device of Embodiment N or Embodiment O, wherein the hydroxypropylmethylcellulose and guar gum are present in the dry composition at a mass ratio of less than or equal to three parts hydroxypropylmethylcellulose to one part guar gum.

Embodiment Q is the device of any one of Embodiments I through P, further comprising a layer of adhesive disposed on the upper surface of the substrate, the adhesive being non-inhibitory to the growth of microorganisms; wherein the a cold-water-reconstitutable coating adhered to the adhesive layer.

Advantages and embodiments of this disclosure are further illustrated by the following examples, but the particular materials and amounts thereof recited in these examples, as well as other conditions and details, should not be construed to unduly limit this disclosure. All materials are commercially available or known to those skilled in the art unless otherwise stated or apparent.

EXAMPLES

Example 1. Preparation of Thin Film Culture Devices

PETRIFILM Aerobic Count (PFAC) Plates were obtained from 3M Company (St. Paul Minn.). Biaxially-oriented polypropylene film (approximately 0.04 mm thick) was obtained from 3M Company. Triphenyl tetrazolium chloride (TTC, part number 17779) was obtained from Sigma (St. Louis, Mo.). Hydroxypropylmethylcellulose (HPMC) powder (Fortefiber HB Ultra, Fortefiber, lot #WK201907F1) was obtained from Dow-Wolff (Bomlitz, Del.). The adhesive used in this Example was as described in Example 1 of U.S. Pat. No. 4,565,783.

Commercially available PFAC had the assembled top film removed and replaced with bi-axially oriented polypropylene (BOPP) top film that had RD-1273 adhesive (3M 927 Adhesive Transfer Adhesive) with 20 µg/mL triphenyl tetrazolium chloride (TTC, Sigma #17779) mixed in with the adhesive. The adhesive was coated to 0.2 g/24 in². The adhesive was then powder-coated to capacity with hydroxypropyl methylcellulose powder/fibers (Fortefiber, lot #WK201907F1; Dow-Wolff Cellulosics; Bomlitz, Del.).

Example 2. Growth of Test Microorganisms on the Thin Film Culture Devices

These culture devices prepared in Example 1 were tested for their ability to support the growth of various species of bacteria (shown in Table 1). Pure cultures of each microorganism were grown over night in tryptic soy broth and were diluted to approximately 50-150 CFU per milliliter in Butterfield's buffer. Thin film culture devices from Example 1 were individually inoculated with 1 mL of the resulting bacterial suspensions. As controls, 1 milliliter aliquots of each suspension was also inoculated into individual PFAC plates. The inoculation procedure for all of the culture devices was as described in the Instructions for Use for the PETRIFILM Aerobic Count Plates available from 3M Company. The inoculated culture devices were incubated for 24 hours at 32° C.

TABLE 1

| Microorganisms used to test the thin film culture devices. |
| --- |
| *Microbacterium esteraeromaticum* |
| *Micrococcus* sp. |
| *Kocuria varians* |
| *Flavoacterium* sp. |
| *Pseudomonas fragi* |
| *Streptococcus aggalactiae* |
| *Staphylococcus aureus* |
| *Escherichia coli* |
| *Bacillus subtilis* |
| *Bacillus amyloliquifaciens* |
| *Lysinibacillus sphaericus* |

After the incubation period, each culture device was observed for the presence (and morphology) of red-colored colonies in the inoculated area of each device. Red-colored colonies, similar in quantity and appearance to those observed on the control plates (with exceptions noted below), were observed for each microorganism listed in Table 2.

TABLE 2

| Organism | Appearance on PFAC control* | Appearance on thin film devices from example 1 |
| --- | --- | --- |
| *Bacillus amyloliquifaciens* | − | +++ |
| *Lysinibacillus sphaericus* | − | +++ |
| *Microbacterium esteraeromaticum* | +++ | +++ |
| *Micrococcus* sp. | +++ | +++ |
| *Kocuria varians* | +++ | +++ |
| *Flavoacterium* sp. | +++ | +++ |
| *Pseudomonas fragi* | +++ | +++ |
| *Streptococcus aggalactiae* | +++ | ++ |
| *Staphylococcus aureus* | +++ | +++ |
| *Escherichia coli* | +++ | +++ |
| *Bacillus subtilis* | +++ | +++ |

*Appearance also included ability to count the colonies to obtain quantitative enumeration (Cfu/ml);
"−" denotes the gel was completely liquefied and a colony count was not possible,
"++" denotes that colonies were easy to observe and count but the colony counts were less than that obtained in a corresponding PFAC control plate;
"+++" denotes sharp colony appearance and colony counts were similar to a corresponding PFAC control.

The PFAC plates inoculated with *Bacillus amyloliquifaciens* and *Lysinibacillus sphaericus* suspensions were observed to have a diffuse pink or red color spread throughout the inoculated area with observable darker-red colonies distributed throughout the area. In addition, the gelling agent in the inoculated area was liquid and, in some instances, the liquid had spread beyond the inoculated area to the edge of the plate. These observations are consistent with the microorganisms having hydrolyzed the gelling agent in the PFAC plates, thereby permitting the bacteria to spread throughout the inoculated area. In contrast, the culture devices of Example 1 that were inoculated with the *Bacillus amyloliquifaciens* and *Lysinibacillus sphaericus* suspensions showed individual colonies growing in the inoculated area, did not have a diffuse pink-red color throughout the inoculated area, and did not show significant loss of viscosity of the cold-water-soluble gelling agents in the inoculated area.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

What is claimed is:

1. A device for growing microorganisms, comprising:
  i. a body member comprising a self-supporting, waterproof substrate having upper and lower surfaces, a layer of adhesive, and a cold-water-soluble powder;
  wherein said layer of adhesive is disposed on said upper surface of said substrate;
  wherein said adhesive is non-inhibitory to the growth of microorganisms;
  wherein said cold-water-soluble powder comprises guar gum and hydroxypropylmethylcellulose and one or more nutrients for growing microorganisms;
  wherein said cold-water-soluble powder is adhered to said adhesive, where said hydroxypropylmethylcellulose and said guar gum are present in said cold-water-soluble powder at a mass ratio in the range of one part of said hydroxypropylmethylcellulose to one part of said guar gum to three parts of said hydroxypropylmethylcellulose to one part of said guar gum; and
  ii. a cover sheet having an inner-facing surface and an outer-facing surface, comprising a dry composition and a layer of adhesive;
  wherein said adhesive is adhered to the inner-facing surface of said cover sheet;
  wherein said dry composition comprises a mixture of hydroxypropylmethylcellulose and guar gum;
  wherein said dry composition is adhered to said inner-facing surface of said cover sheet;
  wherein said device includes a microbial growth zone between said substrate and said cover sheet;
  wherein said microbial growth zone is free of matrices that prevent visualization of bacterial colonies;
  wherein said cover sheet is adhered to said body member so that the upper surface of said substrate faces said inner-facing surface of said cover sheet; and
  wherein said hydroxypropylmethylcellulose and said guar gum are present in said dry composition at a mass ratio in the range of one part of said hydroxypropylmethylcellulose to one part of said guar gum to three parts of said hydroxypropylmethylcellulose to one part of said guar gum.

2. The device of claim 1, the cold-water-soluble powder consists essentially of guar gum and hydroxypropylmethylcellulose.

3. The device of claim 1, wherein the dry composition consists essentially of hydroxypropylmethylcellulose and guar gum.

4. A device for growing microorganisms, comprising:
  i. a body member comprising a self-supporting, waterproof substrate having upper and lower surfaces, and a cold-water-reconstitutable coating;
  wherein said cold-water-reconstitutable coating comprises guar gum and hydroxypropylmethylcellulose and one or more nutrients for growing microorganisms;
  wherein said hydroxypropylmethylcellulose and said guar gum are present in said cold-water-reconstitutable coating at a mass ratio in the range of one part of said hydroxypropylmethylcellulose to one part of said guar gum to three parts of said hydroxypropylmethylcellulose to one part of said guar gum;
  wherein said cold-water-reconstitutable coating is adhered to said substrate; and
  ii. a cover sheet having an inner-facing surface and an outer-facing surface, comprising a dry composition and a layer of adhesive;
  wherein said adhesive is adhered to the inner-facing surface of said cover sheet;
  wherein said dry composition comprises a mixture of hydroxypropylmethylcellulose and guar gum; where said hydroxypropylmethylcellulose and said guar gum are present in said dry composition at a mass ratio in the range of one part of said hydroxypropylmethylcellulose to one part of said guar gum to three parts of said hydroxypropylmethylcellulose to one part of said guar gum
  wherein said dry composition is adhered to said inner-facing surface of said cover sheet;
  wherein said device includes a microbial growth zone between said substrate and said cover sheet;
  wherein said microbial growth zone is free of matrices that prevent visualization of bacterial colonies;
  wherein said cover sheet is adhered to said body member so that the upper surface of said substrate faces said inner-facing surface of said cover sheet.

5. The device of claim 4, wherein the cold-water-reconstitutable coating consists essentially of guar gum and hydroxypropylmethylcellulose.

6. The device of any one of claim 4, wherein the dry composition consists essentially of hydroxypropylmethylcellulose and guar gum.

7. The device of claim 4, further comprising a layer of adhesive disposed on the upper surface of the substrate, the adhesive being non-inhibitory to the growth of microorganisms; wherein the cold-water-reconstitutable coating is adhered to the adhesive layer.

8. The device of claim 1, wherein the cold-water-soluble powder can comprise powdered nutrients and powdered cold-water-soluble gelling agent(s) that are present in a ratio of about 3 parts nutrients: 1 part cold-water-soluble gelling agent(s).

* * * * *